United States Patent [19]

Ogawa et al.

[11] Patent Number: 4,751,290

[45] Date of Patent: Jun. 14, 1988

[54] SIALOSYLCEREBROSIDES

[75] Inventors: Tomoya Ogawa, Musashino; Mamoru Sugimoto, Niiza; Masaaki Numata, Kawagoe; Yoshiyasu Shitori, Tokyo; Masayoshi Ito, Kunitachi, all of Japan

[73] Assignees: Rikagaku Kenkyusho, Wako; Mect Corporation, Tokyo, both of Japan

[21] Appl. No.: 871,289

[22] Filed: Jun. 6, 1986

[30] Foreign Application Priority Data

Jun. 7, 1985 [JP] Japan .................... 60-123951

[51] Int. Cl.$^4$ ............................................ C07H 5/06
[52] U.S. Cl. .................... 536/17.9; 536/17.2; 536/18.4; 536/123
[58] Field of Search ............ 536/17.2, 17.9, 18.4, 536/123

[56] References Cited

U.S. PATENT DOCUMENTS 4,495,346  1/1985  Anderson et al. ................ 536/4.1

OTHER PUBLICATIONS

Chemical Abstracts, vol. 68, No. 3, 15th Jan. 1968, pp. 900–901, Abstract No. 9505e, Columbus, Ohio, US; E. Klenk et al.
"Two Components of a Mixture of Brain Gangliosides," & Hoppeseyler's Z. Physiol. Chem. 348 (10), 1261–1267.
"Handbook of Lipid Research 3, Sphingolipid Biochemistry" Julian N. Kanfer and Sen-itiroh Hakomori, 1983, Plenum Publishing Company.

March, *Advanced Organic Chemistry: Reactions, Mechanisms and Structure*, 1968, p. 664.
Migrdichian, *Organic Synthesis*, vol. 1, 1957, pp. 39 and 429.

*Primary Examiner*—Anton H. Sutto
*Assistant Examiner*—Elli Peselev
*Attorney, Agent, or Firm*—Oblon, Fisher, Spivak, McClelland & Maier

[57] ABSTRACT

This invention provides a novel compound having a formula such as

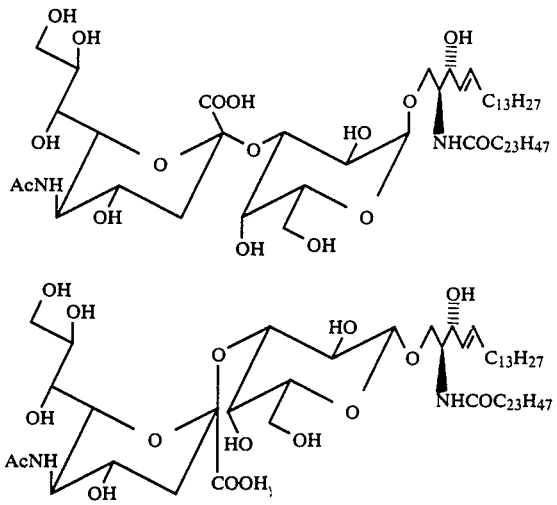

This invention also provides a process for preparing such a compound.

9 Claims, No Drawings

SIALOSYLCEREBROSIDES

BACKGROUND OF THE INVENTION (1) Field of the Invention

This invention relates to sialosylcerebrosides, and more particularly to sialosylcerebrosides contained in ganglioside sphingoglycolipids and a preparation method thereof.

(2) Description of the Prior Art

Glycolipids found in mammal cells are glycosides between ceramides, which are sphingosines (long chain amino alcohols) to which aliphatic acids have been attached through an amide linkage, and one or more sugars such as glucose, galactose, N-acetyl glucosamine, N-acetyl galacotosamine, fucose, sialic acid, etc. Among these glycosides, those containing sialic acid are called gangliosides.

Gangliosides exist mainly in the outer molecular layer of double molecular layers of the mammal cell membrane. Recent studies show that gangliosides play important roles in reception and recognition of, and response to, information in cells, receptor mechanism, differentiation, cell propagation, malignant cell transformation, cell behavior etc.

Among these compounds, sialosylcerebroside $GM_4$ is contained in large amounts in the gray substance of human encephalon and sialosylcerebroside $GM_4$ is considered a distinctive component of myelin membrane. These acidic glycolipids are found in erthrocyte of mouse, renal of rat and yolk of egg.

However, the function of ganglioside glycolipids as a cell membrane component has not been studied sufficiently and it is very difficult to isolate and purify sialosylcerebroside $GM_4$ from an organism. Therefore precise synthesis of such sialosylcerebrosides containing sialosylcerebrosides $GM_4$ is necessary for investigation of the function of ganglioside glycolipids as a cell membrane component.

SUMMARY OF THE INVENTION

An object of this invention is to provide novel sialosylcerebrosides and a preparation method thereof, and a preparation method of sialosylcerebroside $GM_4$.

The novel sialosylcerebrosides of the present invention are represented by the formula I.

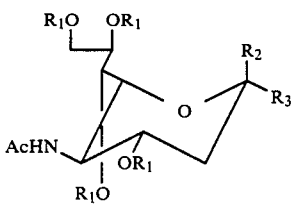

wherein, $R_1$ is hydrogen or acetyl group, $R_2$ is $-COOR_4$ ($R_4$ is hydrogen, sodium or methyl group), and $R_3$ is

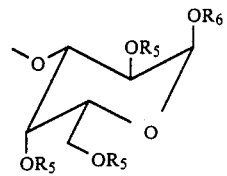

{wherein, $R_5$ is hydrogen or acetyl group, $R_6$ is $-C(CCl_3)=NH$ or

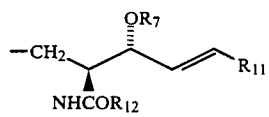

(wherein $R_7$ is hydrogen or benzoyl group, $R_{11}$ is saturated aliphatic hydrocarbon having 10 to 16 carbon atoms and $R_{12}$ is saturated aliphatic hydrocarbon having 15 to 25 carbon atoms)}, or $R_2$ is

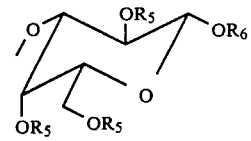

(wherein, $R_5$ and $R_6$ have the same meaning as defined above) and $R_3$ is $-COOR_4$ ($R_4$ has the same meaning as defined above).

DETAILED DESCRIPTION OF THE INVENTION

This invention will now be explained in detail.

(a) Synthesis of ceramide moiety

Ceramide moiety of gangliosides can be prepared by the method as shown in Scheme 1b. Compound (30) can be prepared by the method as shown in Scheme 1a (see the specification of Japanese Patent Application No. 59-44913 (Japanese Patent Public Disclosure No. 60-190745)).

The compound ② can be obtained by refluxing overnight a solution of alkyl halide such as 1-bromotetradecane and triphenylphosphine in a solvent such as xylene.

1,2-O-isopropylidene-α-D-xylo-pentodialdo-1,4-furanose ① is reacted with the compound ② in the presence of BuLi in a solvent such as THF or hexane to prepare the 4-alkylvinyl derivative ③. The reaction temperature and time are suitably $-15°$ C. to $25°$ C. and 0.5 to 24 hours, respectively.

The compound ③ is treated with methanesulfonyl chloride in dry pyridine to produce the 3-methanesulfonyl derivative ④. The reaction is suitably carried out at $0°$ C. to $25°$ C. for 2 to 24 hours.

Treatment of the compound ④ in acetic acid/water removes the isopropylidene group therefrom to yield the diol ⑤. The reaction is suitably carried out at $70°$ to $90°$ C. for 0.5 to 5 hours.

The compound ⑤ is treated with an oxidizing agent such as sodium metaperiodate in a solvent such as ethanol to cut the diol part and then treated with a reducing agent such as sodium borohydride to obtain the diol compound ⑥. The oxidation is carried out at $0°$ C. to 25° C. for 0.5 to 24 hours and the reduction at 0° C. to 10° C. for 0.5 to 2 hours.

The compound ⑥ is reacted with an alkyl vinyl ether such as ethyl vinyl ether in a solvent such as dichloromethane in the presence of a catalyst such as pyridinium p-toluenesulfonate to obtain the di-alkyl vinyl ether ⑦. This reaction is suitably carried out at 0° C. to 30° C. for 0.5 to 24 hours.

The compound 7 is treated an azide such as sodium azide in a solvent such as DMF (dimethylformamide) to obtain the compound ⑧. This reaction is suitably carried out at 70° C. to 120° C. for 15 hours to 6 days.

The azide ⑧ is treated with a reducing agent such as sodium borohydride or Lindler catalyst/$H_2$ in a solvent such as ethanol or isopropanol to obtain the amine ⑨. This reaction is suitably carried out at a reflux temperature for 1 to 6 days when sodium borohydride is used and at 0° C. to 30° C. for 2 to 24 hours at a hydrogen pressure of 1 to 4 atoms when Lindler catalyst/$H_2$ is used.

The amine ⑨ is reacted with an acyl halide in the presence of a basic compound such as pyridine or dimethylaminopyridine to obtain the amide ⑩ or ⑪. This reaction is suitably carried out at 0° C. to 30° C. for 0.5 to 24 hours. Alternatively, the amine ⑨ is dissolved in dichloromethane or the like and reacted with an aliphatic acid in the presence of 2-chloro-1-methylpyridinium iodide, tri-n-butyl amine, etc. to obtain the amide ⑩ or ⑪. This reaction is sufficiently carried out at a reflux temperature for 0.5 to 13 hours in an inert gas atmosphere such as argon.

The amide ⑩ or ⑪ is then treated with pyridinium p-toluenesulfonate, Amberlist A-15 (trademark), etc. in a solvent such as methanol, dichloromethane to remove the protective groups. Thus the ceramide ⑫ or (31) is obtained.

Scheme 1a

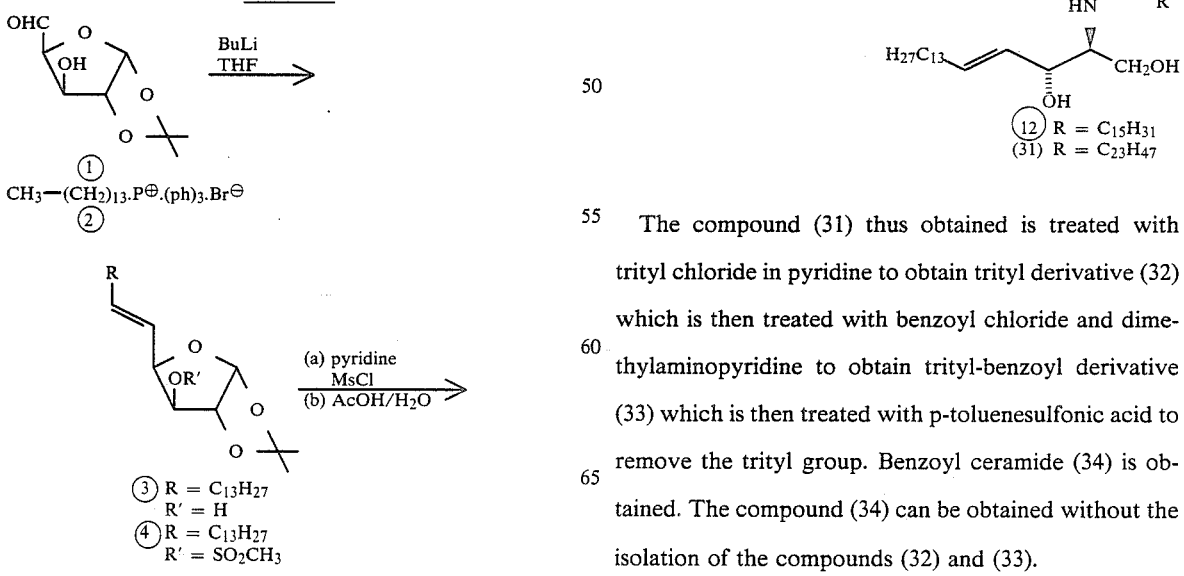

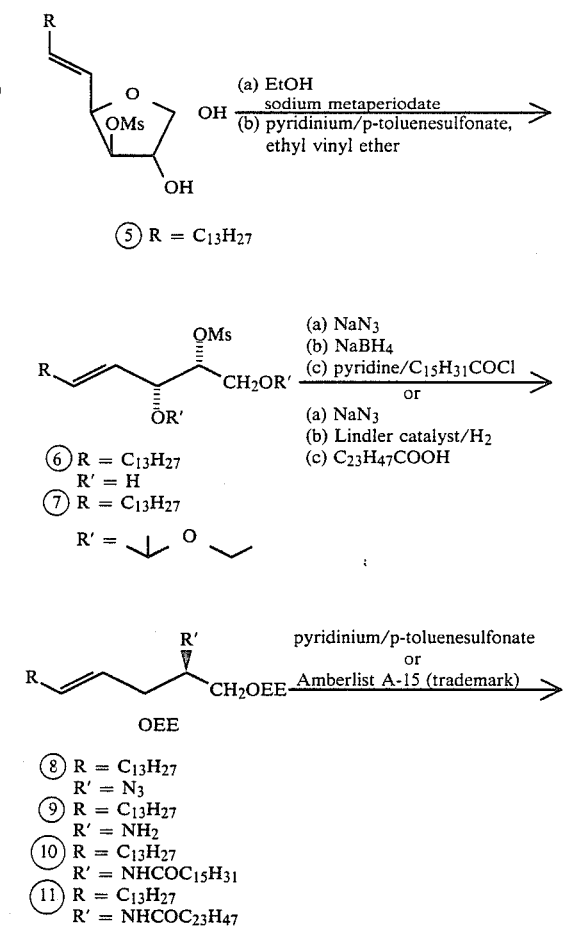

The compound (31) thus obtained is treated with trityl chloride in pyridine to obtain trityl derivative (32) which is then treated with benzoyl chloride and dimethylaminopyridine to obtain trityl-benzoyl derivative (33) which is then treated with p-toluenesulfonic acid to remove the trityl group. Benzoyl ceramide (34) is obtained. The compound (34) can be obtained without the isolation of the compounds (32) and (33).

Scheme 1b

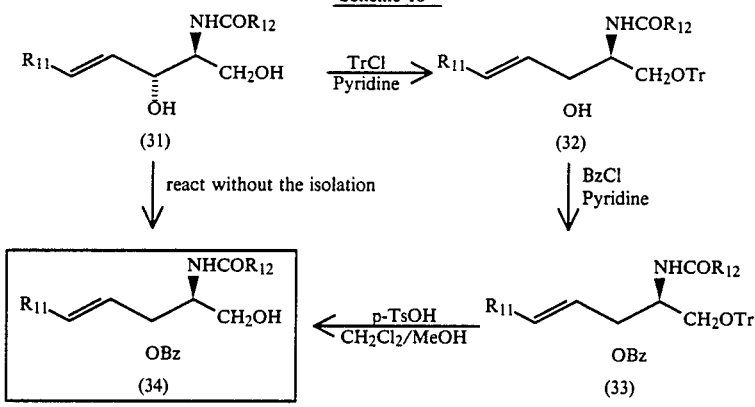

$R_1$: $C_{13}H_{27}$, $R_2$: $C_{23}H_{47}$, Tr: Trityl group, Bz: Benzoyl group (b) Synthesis of sialic acid derivatives (10) and (20)

Sialic acids (10) and (20) which are used to synthesize sialosycerebrosides of the present invention can be obtained by the reaction between the compound (D) obtained from benzylgalactoside (A) as shown in Scheme 2 and N-acetyl neuramic acid acetate methyl ester (compound (E)) synthesized by the Kahn's method.

Benzylgalactoside (A) is suspended in acetone and reacted with 2,2-dimethoxypropane in the presence of p-toluenesulfonic acid to obtain 3,4-0-isopropylidene derivative (B). The derivative (B) is reacted with benzylbromide in DMF in the presence of NaH to obtain tribenzyl derivative (C). The derivative (C) is treated with acetic acid solution to remove isopropylidene group and obtain compound (D). The reaction of the compound (D) and (E) can be carried out suitably in a solvent such as dichloromethane, 1,2-dichloroethane or the like in the presence of a glycosidation catalyst such as $Hg(CN)_2$, $HgBr_2$, molecular sieves (MS), $Ag_2CO_3$, $AgClO_4$, $AgOSO_2CF_3$, $(CH_3)_3COSO_2CF_3$ or the like at $-20°$ to $150°$ C. for 1 to 120 hours.

Scheme 2

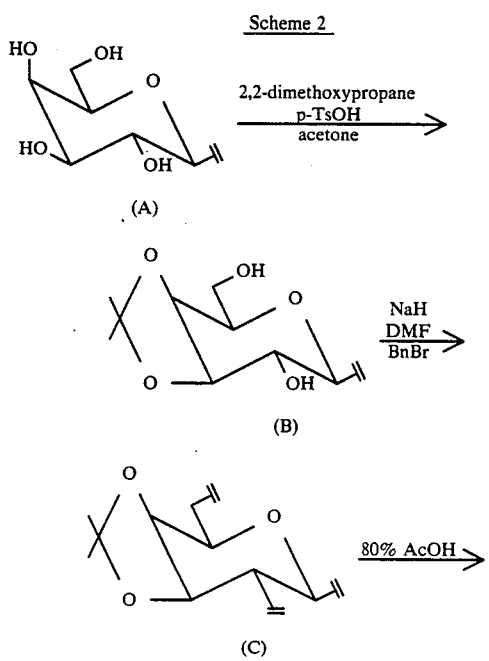

-continued
Scheme 2

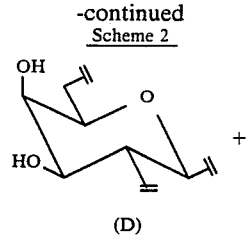

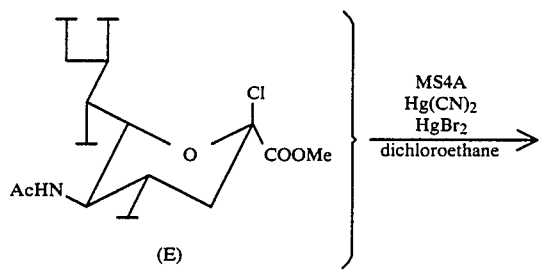

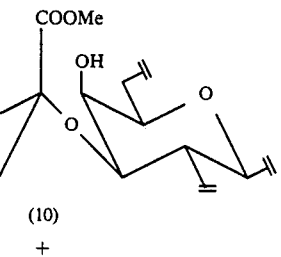

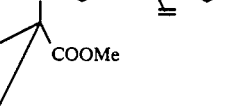

⊣: OAc group (Ac: acetyl)

⊣⊦: OBn group (Bn: benzyl)

(c) Synthesis of sialosylcerebrosides

The sialosylcerebrosides of the present invention can be obtained from sialic acid derivatives (10) and (20) as shown in schemes 3 and 4.

Compound (11) is obtained by acetylation of sialic acid derivative (10) with acetic anhydride and pyridine. Compound (11) is treated with Pd-C and MeOH to remove benzyl group and then the product obtained is acetylated by treating with acetic anhydride and pyridine to obtain compound (12). Then compound (12) is treated with $NH_2NH_2AcOH$ and DMF to obtain deacetylated compound (13).

Compound (13) is reacted with trichloroacetonitrile in a solvent such as methylene chloride or the like in the presence of NaH to obtain compound (14). This reaction may be carried out, for example, at a temperature $-10°$ to $30°$ C., preferably under ice cooling condition, for 1 to 5 hours under agitation.

Compound (14) is reacted with benzoyl derivative of ceramide (Bz ceramide) (34), for example, in a solvent such as chloroform or the like in the presence of MS4A and $BF_4.EtO_2$ to obtain compounds (15) and (16). This reaction may be carried out at a temperature of $-40°$ to $40°$ C. for 0.5 to 2 hours, then at a temperature of $0°$ to $40°$ C. for 2 to 24 hours under agitation. Compounds (15) and (16) can be separated by a method such as silica gel column chromatography.

Compounds (17) and (18) can be obtained by, for example, treating compounds (15) and (16) respectively with NaOMe in a solvent such as MeOH/THF or the like and treating the resultant product with Amberlist IRC50 or the like if necessary. The treatment with NaOMe is preferably carried out at a temperature of $0°$ to $30°$ C. for 0.5 to 6 hours.

On the other hand, sialic acid derivative (20) is acetylated with 4-dimethoxyaminopyridine in a mixture of pyridine and acetic anhydride to obtain compound (21). Compound (21) is treated with Pd-C and MeOH to remove benzyl group therefrom and obtain compound (22). Compound (22) is acetylated by treating with 4-dimethoxyaminopyridine in a mixture of pyridine and acetic anhydride to obtain compound (23). Compound (23) is treated with $NH_2NH_2AcOH$ in DMF to remove acetyl group therefrom and obtain compound (24).

Compound (24) is reacted with trichloroacetone, for example, in a solvent such as dichloroethane or the like in the presence of DBU to obtain compound (25). This reaction may be carried out at a temperature of $-10°$ to $30°$ C. for 30 minutes to 6 hours.

Compound (25) is reacted with a benzoyl derivative of ceramide (IV), for example, in a solvent such as chloroform or the like in the presence of MS and $BF_3.Et_2O$ to obtain compound (26). This reaction may be carried out under agitation at a temperature of $-10$ to $40$, preferably $0°$ to $20°$ C., for 2 to 5 hours, followed by additional agitation at a temperature of $20°$ to $40°$ C. for 1 to 24 hours.

Scheme 3
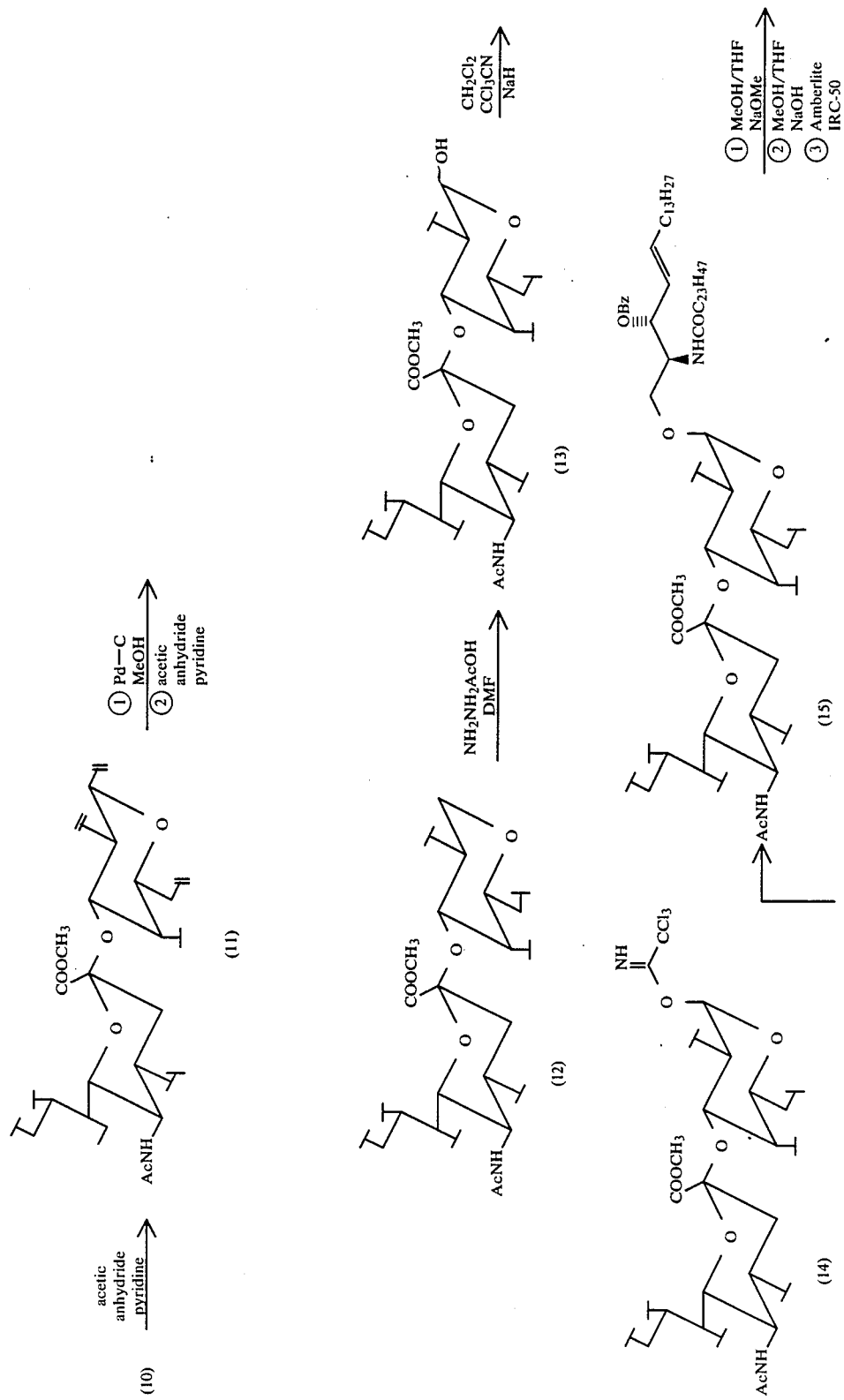

-continued
Scheme 3
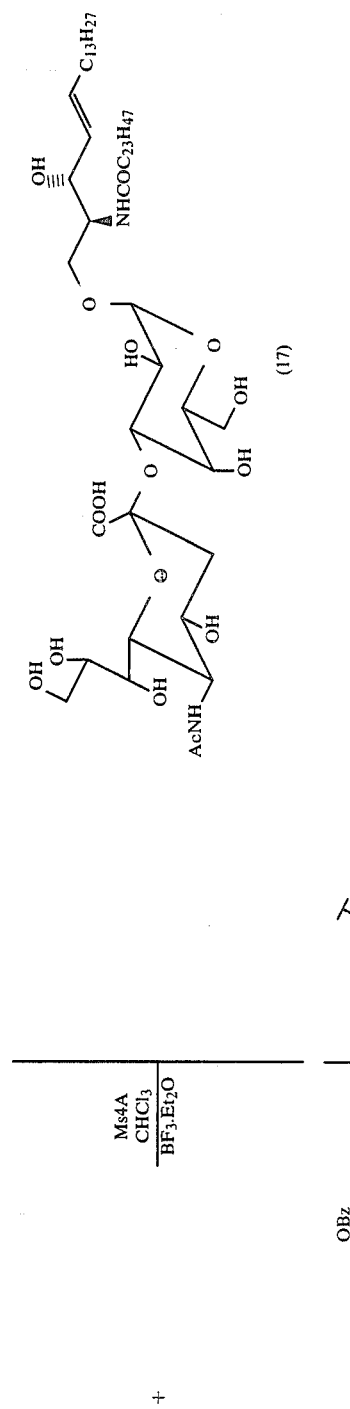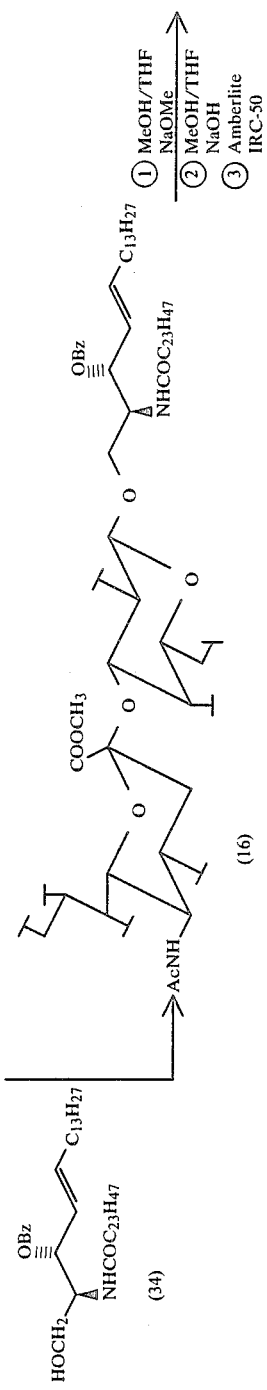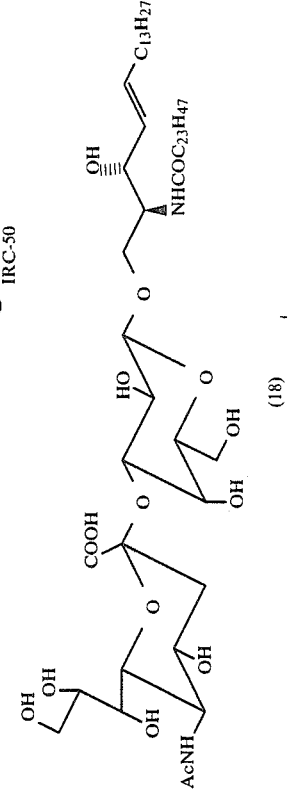
†: Ac group
††: OBn group

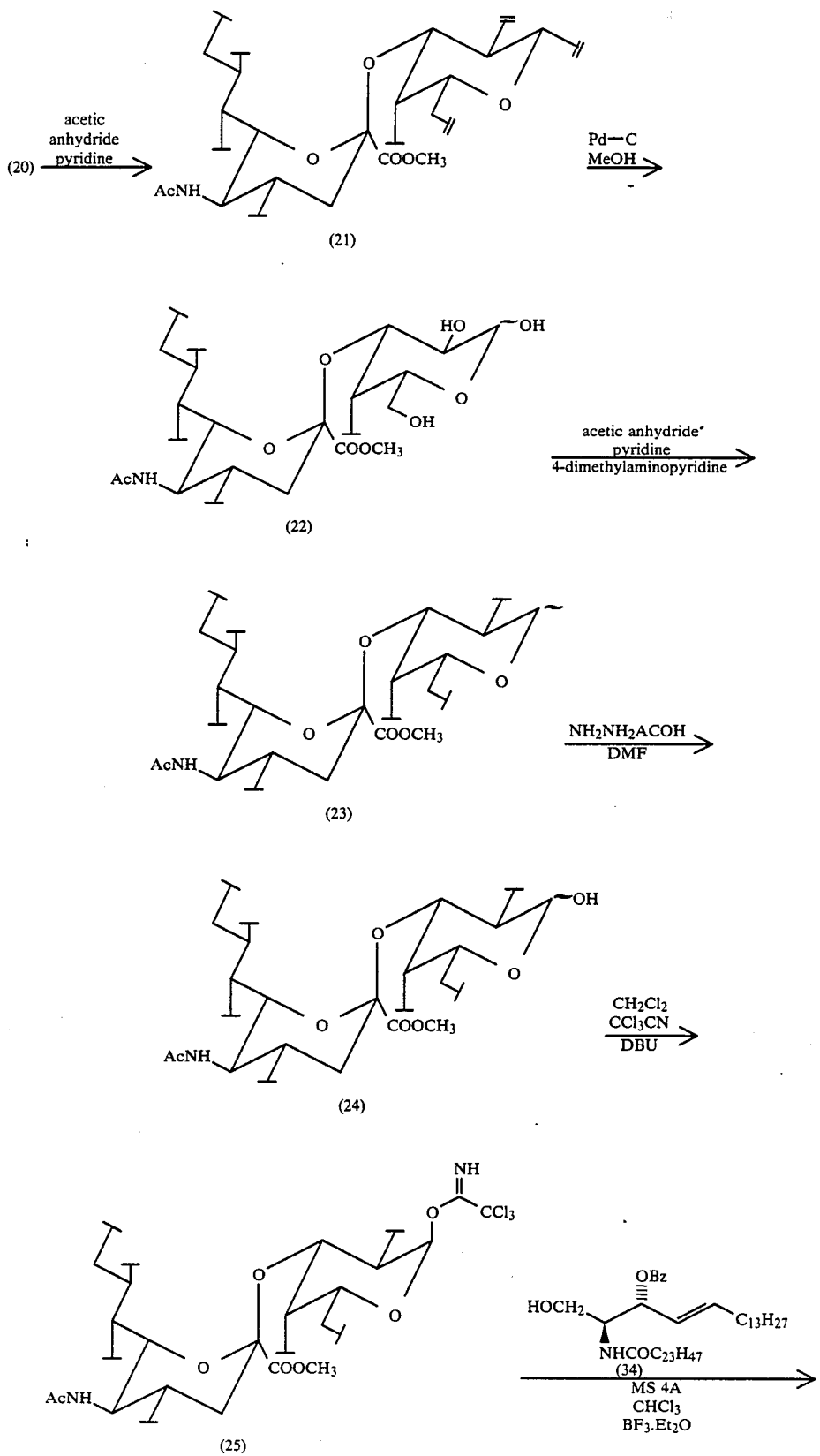

-continued
Scheme 4

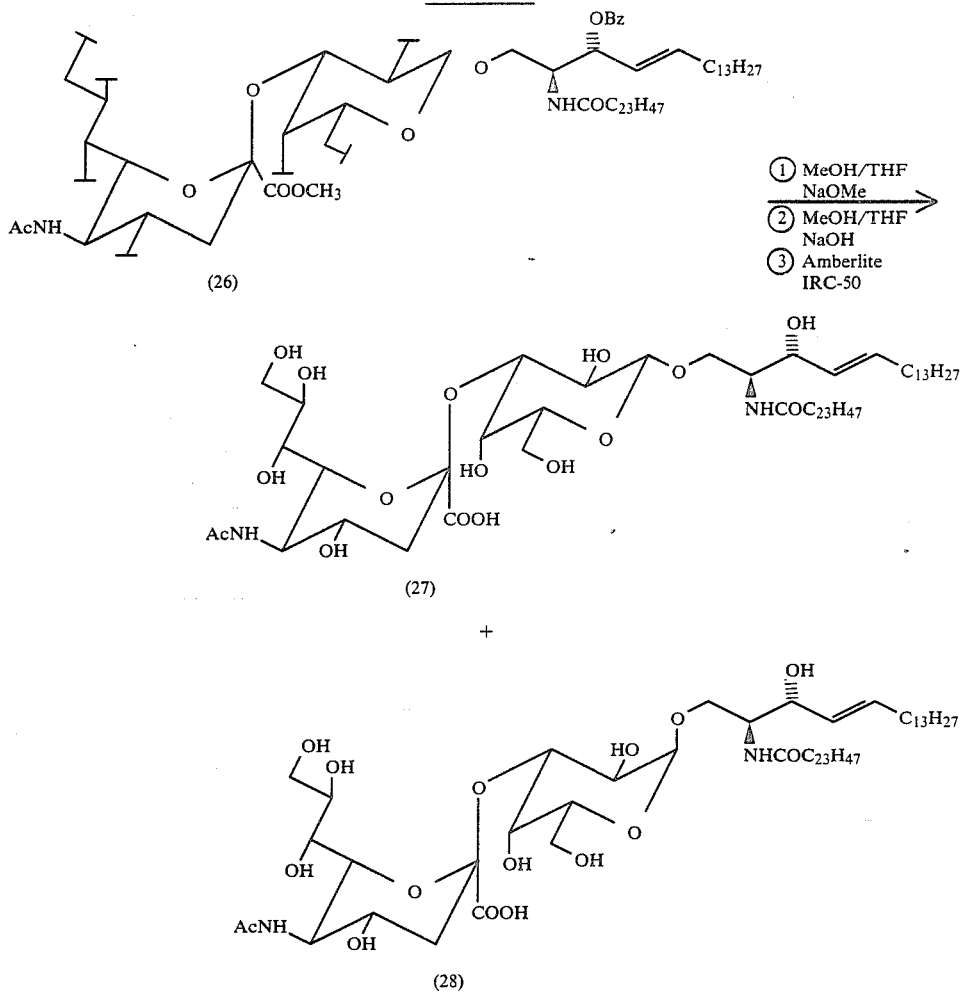

Compound (26) is treated with NaOCH₃ in a solvent such as a mixture of THF and MeOH or the like to remove benzyl group and obtain compound (27). This treatment may be carried out under agitation of the solution containing compound (26) at a temperature of 0° to 40° C. for 1 to 24 hours. The treatment procedure can include an additional treatment with H₂O in a mixture of THF and MeOH and neutralization of the solution with Amberlite IRC-50.

Compounds (14), (15), (16), (17), (25), (26) and (27) obtained by the method of the present invention are novel compounds.

USEFULNESS OF THE INVENTION

The novel compounds of the present invention are useful as a tumor marker, a differentiation marker for cells having inducing ability of differentiation and synthesis intermediates thereof.

EXAMPLE

The present invention will now be illustrated in detail by following the examples.

REFERENCE EXAMPLE 1

From Compound (11) to Compound (12)

658 mg (0.68 mmol) of compound (11) was dissolved in 25 ml of methanol and reduced catalytically using 320 mg of 10% Pd-C at room temperature for 24 hours. After the reaction, the reaction mixture was filtrated to remove Pd-C and the mother liquid obtained was concentrated under reduced pressure. The residue obtained (463 mg, 98%, Rf 0.72, BuOH:EtOH:H₂O=4:2:2) was dissolved in a mixture of 2 ml of acetic anhydride and 2 ml of pyridine, agitated at room temperature for 24 hours and concentrated under reduced pressure. The residue was purified by silica gel column (Wakogel C-300, 35 g, toluene:ethyl acetate=1:4) to obtain 545 mg of compound (12) (yield: 85%).

$[\alpha]_D^{22}+7.60$ (C=0.96, CHCl₃)

Rf=0.38, EtOAc, HPTLC.

Elemental analysis: Calculation: C, 49.69, H, 5.77, N, 1.70; Found: C, 49.73, H, 5.78, N, 1.57.

NMR: (400 MHz ppm, CDCl₃, TMS), 1.71, 1H, t, J=12.5, H-3bax, 2.60, 1, H, m .H-3beq 1.86-2.23 27 H, CH₃CO, 3.86, S, —OCH₃ α-anomer, 3.85 S, —OCH₃ β-anomen, 5.38 d, J=8.3 H-1aβ 6.29 H-1aα d, J=3.91

REFERENCE EXAMPLE 2

From Compound (12) to Compound (13)

452 mg (0.55 mmol) of compound (12) was dissolved in 1.0 ml of DMf, heated to 50° C., added with 56 mg of NH₂NH₂AcOH and agitated for 5 minutes. After the reaction mixture was cooled, the mixture was diluted with ethyl acetate and washed with water. Ethyl acetate phase was dried with MgSO₄ and concentrated to obtain 414 mg of compound (13) (yield: 97%). Rf=0.32 EtOAc, HPTLC.

EXAMPLE 1

From Compound (13) to Compound (14)

156 mg of compound (13) was dissolved in 1.0 ml of methylene chloride and added with 116 mg (0.80 mmol) of trichloroacetonitrile. The mixture obtained was added with 9.0 mg of NaH (60%-oily) under agitation while cooling by an ice bath and agitated additionally for 3 hours. The reaction mixture was concentrated under reduced pressure and purified by using silica gel column (Wakogel C-300, 10 g, EtOAc) to obtain 84 mg of compound (14) (yield: 45%).

Rf=0.37, EtOAc.

EXAMPLE 2

From Compound (14) to Compounds (15) and (16)

62 mg (0.067 mmol) of compound (14) and 51 mg (0.067 mmol) Bz-ceramide compound (34) prepared by the method as shown in Scheme 1a and 1b were dissolved in 2 ml of chloroform. The chloroform solution was added with 1 g of activated M.S.4A AW300 and added with 10 μl (0.08 mmol) of BF₃.Et₂O under agitation while cooling by an ice bath. The reaction mixture was agitated at the same temperature for 1 hour and agitated at room temperature for 24 hours. Then the reaction mixture was diluted with chloroform, filtered with selliate and concentrated under reduced pressure. The residue was purified by using silica gel column (Wakogel C-300, 20 g, toluene:ethyl acetate=1:2) to obtain 10.4 mg of compound (15)(yield: 10.2%) and 28 mg of compound (16) (yield: 27.5%).

Compound (15)

Rf=0.41 (toluene:ethyl acetate=1:2).

Elemental analysis: Calculation: C, 64.18 H, 8.64 N, 1.85; Found: C, 64.14 H, 8.71 N, 1.87.

$[\alpha]_D^{20}$ −17.2 (C=0.92, CHCl₃).

NMR: (400 MHz ppm CDCl₃ TMS) 0.876 CH₃ t J=5.9, 0.879, CH₃t J=5.4, 1.252 CH₂ 1.917–2.165 CH₃CO, 3.830 CH₃O-, S.

Compound (16)

RF=0.25 (toluene:ethyl acetate=1:2).

$[\alpha]_D^{21}$ −0.37 (C=1.40, CHCl₃).

Elemental analysis: C₈₁H₁₃₀N₂O₂₄+½C₆H₅CH₃; Calculation: C, 64.98 H, 8.64 N, 1.79; Found: C, 65.07 H, 8.77 N, 2.05.

EXAMPLE 3

From Compound (15) to Compound (17)

25 mg (0.0165 mmol) of compound (15) was dissolved in 2.0 ml of a mixture of THF and MeOH (THF:MeOH=1:1), added with 70 μl of 2.14N NaHCO₃ aqueous solution and agitated at room temperature for 3 hours. The reaction mixture was concentrated under reduced pressure and the residue was added with 1.0 ml of THF and 1.0 ml of water and agitated at room temperature for 1 hour. The mixture obtained was neutralized by using Amberlite IRC50 and the Amberlite was removed by filtration. The filtrate was dried under the reduced pressure. The residue was dissolved in 2.0 ml of a mixture of THF and MeOH (THF:MeOH=1:1). The mixture was made basic with a NaOH aqueous solution and concentrated under reduced pressure. The residue was dissolved in a mixture of chloroform, methanol and water (60:30:4.6) and purified by using Sephadex LH-20 column (1×45 cm) to obtain 12 mg of compound (17) (yield: 66%).

Rf=0.34, chloroform:methanol:water=60:30:4.6.

NMR (400 MHz d.b DMSO 30° TMS) 5.54, H-5', t.d. J=6.0, 16.4; 5.55, H-4', d, d, J=7.0, 15.6, 4.66, bs H-1a eq, 4.22, H-3a, dd J=4.0, 7.0, 3.98 H-4a , J=2.4, 3.90 H-3' t J=7.0 1.23, s CH₂ 0.85, CH₃, t J=6.4.

EXAMPLE 4

From Compound (16) to Compound (18)

10 mg (0.066 mmol) of compound (16) was dissolved in 2 ml of a mixture of THF and MeOH (1:1). The solution obtained was added with 15 μl of n NaOCH₃ and agitated overnight at room temperature. The reaction mixture was added with 10 μl of 1NNaOCH₃ and agitated at room temperature for 4 hours. Then the solvent of the reaction mixture was removed under reduced pressure. The residue was added with 2 ml of a mixture of THF and MeOH (1:1) and 0.5 ml of H₂O and agitated overnight at room temperature. The solvent of the mixture was removed under reduced pressure. The residue was purified by using Sephadex LH-20 column (CHCl₃:MeOH:H₂O=60:30:4.6) to obtain 5 mg of compound (18) (yield: 68.5%).

Rf=0.386 (CHCl₃:MeOH:H₂O=60:30:4.6).

$[\alpha]_D^{23}$ −2.545 (C=0.165, CHCl₃:MeOH=2:1).

NMR (400 MHz d-b DMSO, 30° TMS) 5.52, H-5', d t, J=6.6, 15.1; 5.34, H-4', d d, J=15.4, 7.1; 4.07, H-1, aax J=7.6 2.76, H-3beq, dd, J=12.5, 4.9.

REFERENCE EXAMPLE 3

From Compound (20) to Compound (21)

3 ml of pyridine and 3 ml of acetic anhydride were added to 150 mg (0.16 mmol) of compound (20) and the compound was dissolved therein. The mixture obtained was added with 50 mg of 4-dimethoxyaminopyridine and agitated at room temperature for 2 days. The solvent contained in the reaction mixture was removed to obtain the residue and the residue was purified by column chromatography (Wakogel C-300, 20 g, toluene:MeOH=10:1) to obtain 180 mg of compound (21) (yield: 89%).

Rf=0.439 (toluene:MeOH=10:1).

$[\alpha]_D^{19}$ −19.29 (C=0.985, CHCl₃).

REFERENCE EXAMPLE 4

From Compound (21) to Compound (22)

1.1449 g of compound (21) was dissolved in 50 mg MeOH and reduced catalytically by using 600 mg of 10% Pd-C at room temperature for 4 hours. The reaction mixture was filtered through selliate and distilled under reduced pressure to obtain 807 mg of compound (22) (yield: 97.9%).

Rf=0.64 (BuOH:EtOH:H₂O=4:2:1).

REFERENCE EXAMPLE 5

From Compound (22) to Compound (23)

121 mg (0.174 mmol) of compound (22) was dissolved in a mixture of 3 ml of pyridine and 3 ml of acetic anhydride, added with 20 mg of 4-dimethoxyaminopyridine and agitated overnight. The reaction mixture was distilled under reduced pressure and the residue was purified by column chromatography (C-300, 20 g, toluene:-

MeOH=10:1) to obtain 110.4 mg of compound (23) (yield: 72.2%).

Rf=0.259 (toluene:MeOH=10:1).

$[\alpha]_D^{19}+26.63$ (C=0.995, CHCl$_3$).

Elemental analysis: $C_{34}H_{47}O_{22}N_1+\frac{1}{2}C_6H_5CH_3$; Calculation: C, 51.90%, H, 5.92%, N, 1.61; Found: C, 51.71%, H, 5.91%, N, 1.69.

REFERENCE EXAMPLE 6

From compound (23) to Compound (24)

96 mg (0.12 mmol) of compound (23) was dissolved in 1 ml of DMF, added with 12.2 mg of H$_2$N.NH$_2$.AcOH and agitated at 50° C. for 5 minutes. The reaction mixture was added with ethyl acetate and washed with water. The mixture obtained was dried with dried magnesium sulfate and distilled under reduced pressure. The residue was purified by column chromatography (C-300, 25 g, acetone:carbon tetrachloride=1:1) to obtain 69.5% of compound (24) (yield=76.4%).

Rf=0.509 (acetone:carbon tetrachloride).

$[\alpha]_D^{19}+36.16$ (C=1.015, CHCl$_3$).

EXAMPLE 5

From Compound (24) to Compound (25)

133 mg (0.17 mmol) of compound (24) was dissolved in 1 ml of dried dichloroethane, added with 0.358 ml of Cl$_3$CCN and 12 μl (0.085 mmol) of DBU while cooling by an ice bath and agitated additionally for 3 hours. The reaction mixture was purified by column chromatography (C-300, 20 g, acetone:carbon tetrachloride=1:2) to obtain 122 mg of compound (25) (yield: 77.4%).

Rf=0.393 (acetone:carbon tetrachloride=1:2).

$[\alpha]_D^{19}+35.18$ (C=1.00, CHCl$_3$).

EXAMPLE 6

From Compound (25) to Compound (26)

100 mg (0.108 mmol) of compound (25) and 83 mg (0.109 mmol) of Bz-ceramide dissolved in 3 ml of chloroform were added with 1 g of MS (acid resistance). The mixture was added with 15 μl (0.124 mmol) of BF$_3$.Et$_2$O while cooling by an ice-MeOH bath, and agitated at the same temperature for 1 hour, and room temperature for 24 hours. The reaction mixture was filtered through selliate and distilled under reduced pressure. The residue was purified by column chromatography (C-300, 20 g, toluene:ethyl acetate=1:2) to obtain 20.9 mg of compound (26) (yield: 12.7%).

Rf=0.25 (toluene:ethyl acetate=1:2)

$[\alpha]_D^{18}+8.80$ (C=0.25, CHCl$_3$).

Elemental analysis: Calculation C, 64.18, H, 8.64, N, 2.05;

Found: C, 64.03, H, 8.50, N, 1.80.

EXAMPLE 7

From Compound (26) to Compound (27)

15 mg (0.0989 mmol) of compound (26) was dissolved in a mixture of 1 ml of THF and 1 ml of MeOH, added with 25 μl of 1N NaOCH$_3$ and agitated overnight at room temperature. After the vacuum distillation of the reaction mixture, the residue obtained was added with 1 ml of THF, 1 ml of MeOH and 0.5 ml of water and agitated overnight at room temperature. The reaction mixture was neutralized by Amberlite IRC-50, filtered and distilled under reduced pressure. The residue was purified by TLC (developed by CHCl$_3$:MeOH:H$_2$O=60:30:4.6 and extracted by CHCl$_3$:MeOH:H$_2$O=5:5:1) and Sephadex LH-20 (CHCl$_3$:MeOH:H$_2$O=60:30:4.6) to obtain 7.3 mg of compound (27) (yield: 67%) and 2.5 mg of compound (28) (yield: 23%).

Compound (28)

Rf=0.412 (CHCl$_3$:MeOH:H$_2$O=60:30:4.6).

$[\alpha]_D^{24}+15.60$ (C=0.125, CHCl$_3$:MeOH=2:1).

NMR (400 MHz d-b DMSO 650 TMS); 5.56, H-5' d,t, J=15.1, 7.1. 5.37, H-4' d,d, J=15.4, 6.6; 4.67 H-1aeq bs; 4.10, H-4a bs.

Compound (27)

Rf=0.333 (CHCl$_3$:MeOH:H$_2$O=60:30:4.6).

$[\alpha]_D^{24}-13.34$ (C=0.365, CHCl$_3$:MeOH=2:1).

NMR (400 MHz d-b DMSO 65° TMS) 5.54, H-5' d,t, J=1.54, 6.6; 5.39 H-4' d,d, J=6.8, 15.6; 4.06 H-1aax d, J=7b; 4.03 H-4a bs.

We claim:

1. A sialosylcerebroside of formula I:

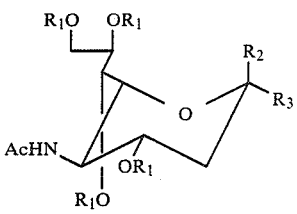

wherein R$_1$ is hydrogen or acetyl, R$_2$ is —COOR$_4$, wherein R$_4$ is hydrogen, sodium or methyl, and R$_3$ is

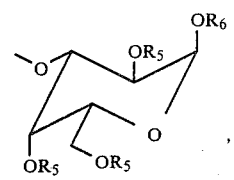

wherein R$_5$ is hydrogen or acetyl, R$_6$ is —C(CCl$_3$)=NH or

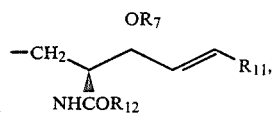

wherein R$_7$ is hydrogen or benzoyl, R$_{11}$ is a saturated aliphatic hydrocarbon group having 10 to 16 carbon atoms and R$_{12}$ is a saturated aliphatic hydrocarbon group having 15 to 25 carbon atoms; or R$_2$ is

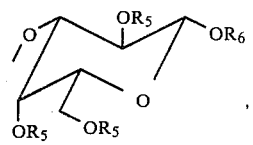

wherein R$_5$ and R$_6$ have the same meaning as defined above and R$_3$ is —COOR$_4$, wherein R$_4$ has the same meaning as defined above.

2. The sialosylcerebroside of claim 1, wherein R$_2$ is —COOR$_4$, wherein R$_4$ is hydrogen, sodium or methyl, and R$_3$ is

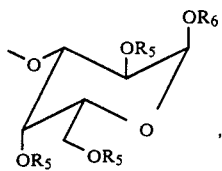

wherein $R_5$ is hydrogen or acetyl or $R_6$ is $-C(CCl_3)=NH$.

3. The sialosylcerebroside of claim 2, wherein $R_1$ and $R_5$ are each acetyl and $R_4$ is methyl.

4. The sialosylcerebroside of claim 3, wherein $R_6$ is

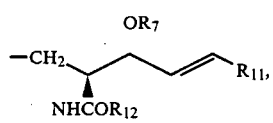

wherein $R_7$ is benzoyl, $R_{11}$ is a saturated aliphatic hydrocarbon group of 10 to 16 carbon atoms and $R_{12}$ is a saturated aliphatic hydrocarbon group of 15 to 25 carbon atoms.

5. The sialosylcerebroside of claim 2, wherein $R_1$, $R_4$ and $R_5$ are each hydrogen and $R_6$ is

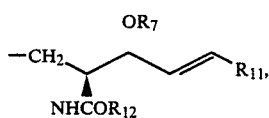

wherein $R_7$ is hydrogen, and $R_{11}$ and $R_{12}$ are as defined in claim 4.

6. The sialosylcerebroside of claim 1, wherein $R_2$ is

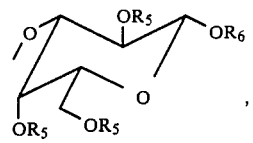

wherein $R_5$ is hydrogen or acetyl and $R_6$ is $-C(CCl_3)=NH$ and $R_3$ is $-COOR_4$, wherein $R_4$ is hydrogen, sodium or methyl.

7. The sialosylcerebroside of claim 6, wherein $R_1$ and $R_5$ are each acetyl and $R_4$ is methyl.

8. The sialosylcerebroside of claim 7, wherein $R_6$ is

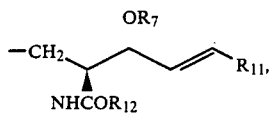

wherein $R_7$ is benzoyl and $R_{11}$ and $R_{12}$ are as defined in claim 1.

9. The sialosylcerebroside of claim 6, wherein $R_1$, $R_4$ and $R_5$ are each hydrogen and $R_6$ is

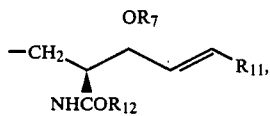

wherein $R_7$ is hydrogen and $R_{11}$ and $R_{12}$ are as defined in claim 1.

* * * * *